United States Patent [19]
Roshdy

[11] Patent Number: 5,601,189
[45] Date of Patent: Feb. 11, 1997

[54] FOLDER PACKAGE FOR ELECTROSURGICAL SCISSORS

[75] Inventor: Constance Roshdy, New Egypt, N.J.

[73] Assignee: Ethicon, Inc., Somerville, N.J.

[21] Appl. No.: 649,151

[22] Filed: May 17, 1996

[51] Int. Cl.⁶ .................................................. B65D 73/00
[52] U.S. Cl. ........................................ 206/363; 206/482
[58] Field of Search .................................. 206/349, 363, 206/438, 476, 477, 482, 483, 495

[56] References Cited

U.S. PATENT DOCUMENTS

| | | | |
|---|---|---|---|
| 4,506,787 | 3/1985 | Bruso | 206/363 |
| 5,234,106 | 8/1993 | Transue et al. | 206/363 |

Primary Examiner—Jacob K. Ackun
Attorney, Agent, or Firm—Emil Richard Skula

[57] ABSTRACT

A folder package for a electrosurgical scissors. The package has a base panel having a pair of substantially opposed major sides and a pair of substantially opposed minor sides. Foldably connected to a top minor side of the base panel is a scissors retention panel. The scissors retention panel is preferably foldably connected along a crushed fold line. The scissors retention panel has a base or bottom section, and an intermediate middle section and a top. The scissors retaining panel has a pair of opposed outwardly extending tab panels. Each tab panel has a pair of crushed fold lines contained therein. Extending from the top of the scissor retaining panel is a tab member. The tab has a U-shaped slit forming a retention tab and an opening. An additional slit at the end of the tab member intersects the U-shaped slit and divides the end of the tab member adjacent to the top of the U-shaped slit into opposed L-shaped members.

8 Claims, 3 Drawing Sheets

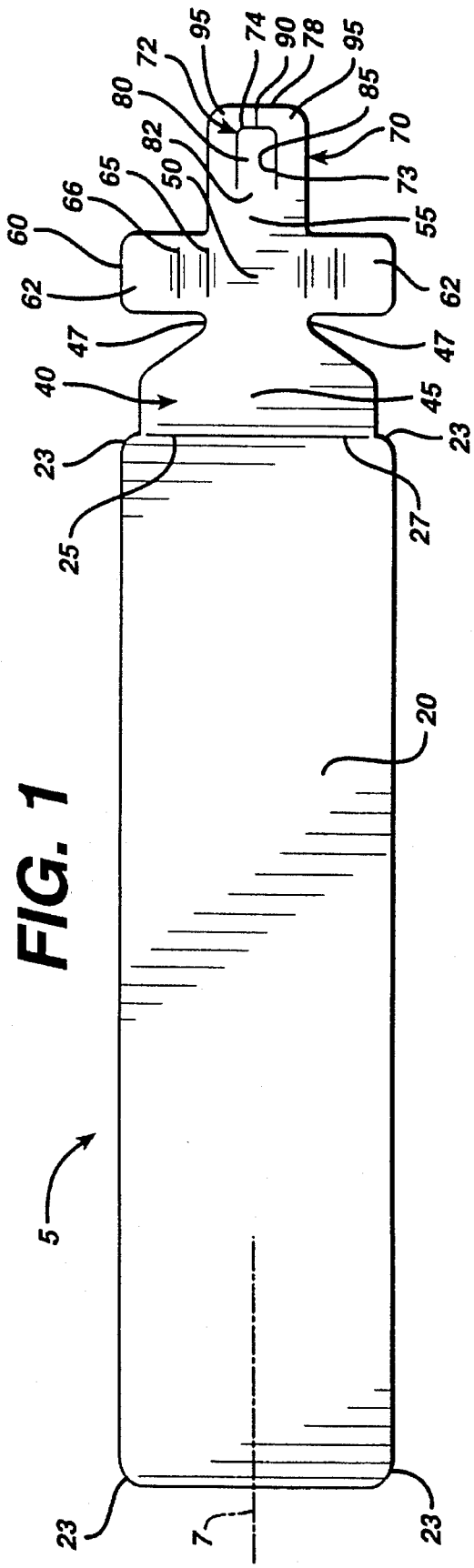
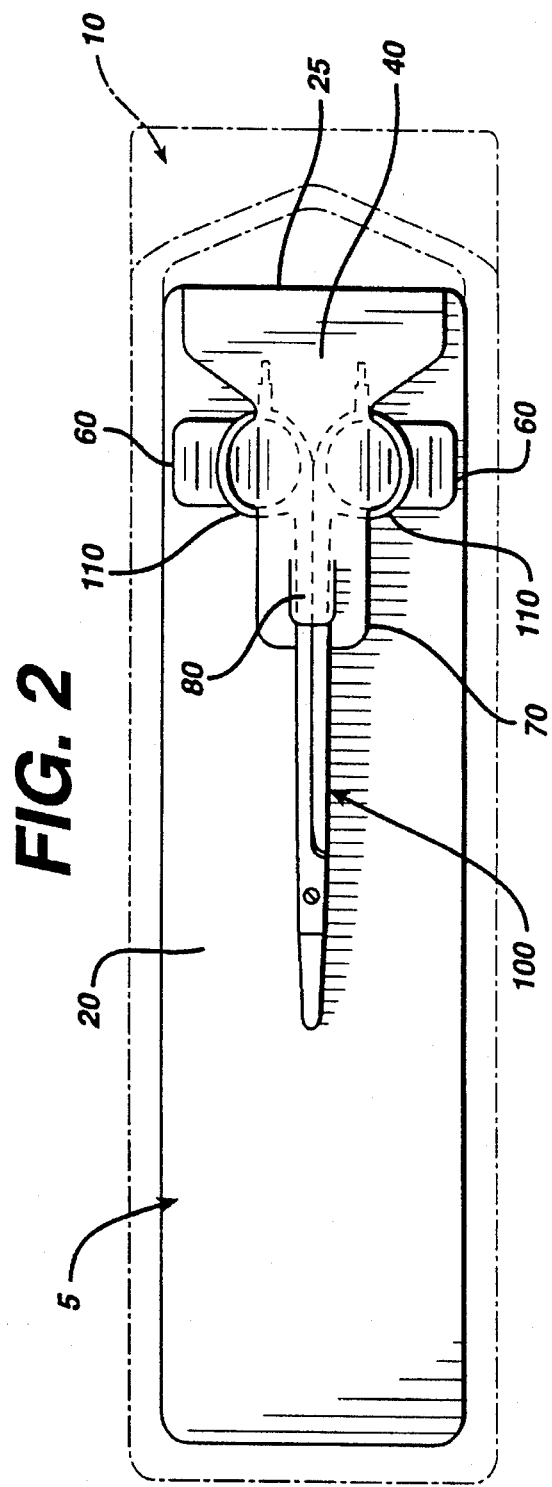
FIG. 1
FIG. 2

1

FOLDER PACKAGE FOR ELECTROSURGICAL SCISSORS

TECHNICAL FIELD

The field of art to which this invention pertains is packaging, in particular, folder packages for scissors.

BACKGROUND OF THE INVENTION

Surgical scissors are well known in the surgical arts for use in various surgical procedures. The scissors are conventionally shipped in bulk or simply placed in boxes with conventional packing materials to prevent the scissors from moving or contacting each other during shipping, handling and storage. Recently, electrosurgical scissors have been developed for use in electrosurgical procedures. The electrosurgical scissors combine the advantages of mechanical shearing-type cutting along with electrosurgical hemostasis and cutting. These scissors require special packaging since they typically have electrodes, insulated exteriors and special non-conductive shearing surfaces which must be protected from damage during shipping, handling and storage. Electrosurgical scissors are disclosed in U.S. Pat. No. 5,324,289 which is incorporated by reference.

Accordingly, there is a need in this art for packages for electrosurgical scissors which protect the scissors during shipping and handling. There is a further need for such packages wherein the scissor is readily removed from the scissor package.

DISCLOSURE OF THE INVENTION

It is an object of the present invention to provide a package for electrosurgical scissors which protects the scissor from damage during shipping, handling and storage.

It is a further object of the present invention to provide a package which is inexpensive and easily assembled.

It is yet a further object of the present invention to provide a package for electrosurgical scissors wherein the scissors are easily removed from the package.

Therefore, a folder package for electrosurgical scissors is disclosed. The package has a base panel having a pair of substantially opposed major sides and a pair of substantially opposed minor sides. Foldably connected to a top minor side of the base panel is a scissors retention panel. The scissor retention panel is preferably foldably connected along a crushed fold line. The scissors retention panel has a base section and an intermediate section and a top. The scissors retention panel has a pair of opposed outwardly extending tab panels. The tab panels extend out from the intermediate section of the retention panel. Each tab panel has a pair of crushed fold lines contained therein. Extending from the top of the scissors retention panel is a tab member. The tab member has a U-shaped slit therein forming a retention tab and an opening. An additional slit at the end of the tab member intersects the U-shaped slit and divides the end the tab member adjacent to the top of the U-shaped slit into opposed L-shaped members.

Yet another aspect of the present invention is the above described package containing an electrosurgical scissors instrument.

Other features and advantages of the invention will become more apparent from the following description and accompanying drawings.

BRIEF DESCRIPTION OF THE DRAWINGS

FIG. 1 is a plan view of an unassembled package of the present invention.

FIG. 2 is a plan view of an assembled package of the present invention containing scissors wherein the package and electrosurgical scissors are placed in an outer envelope or pouch.

BEST MODE FOR CARRYING OUT THE INVENTION

Figure 3:
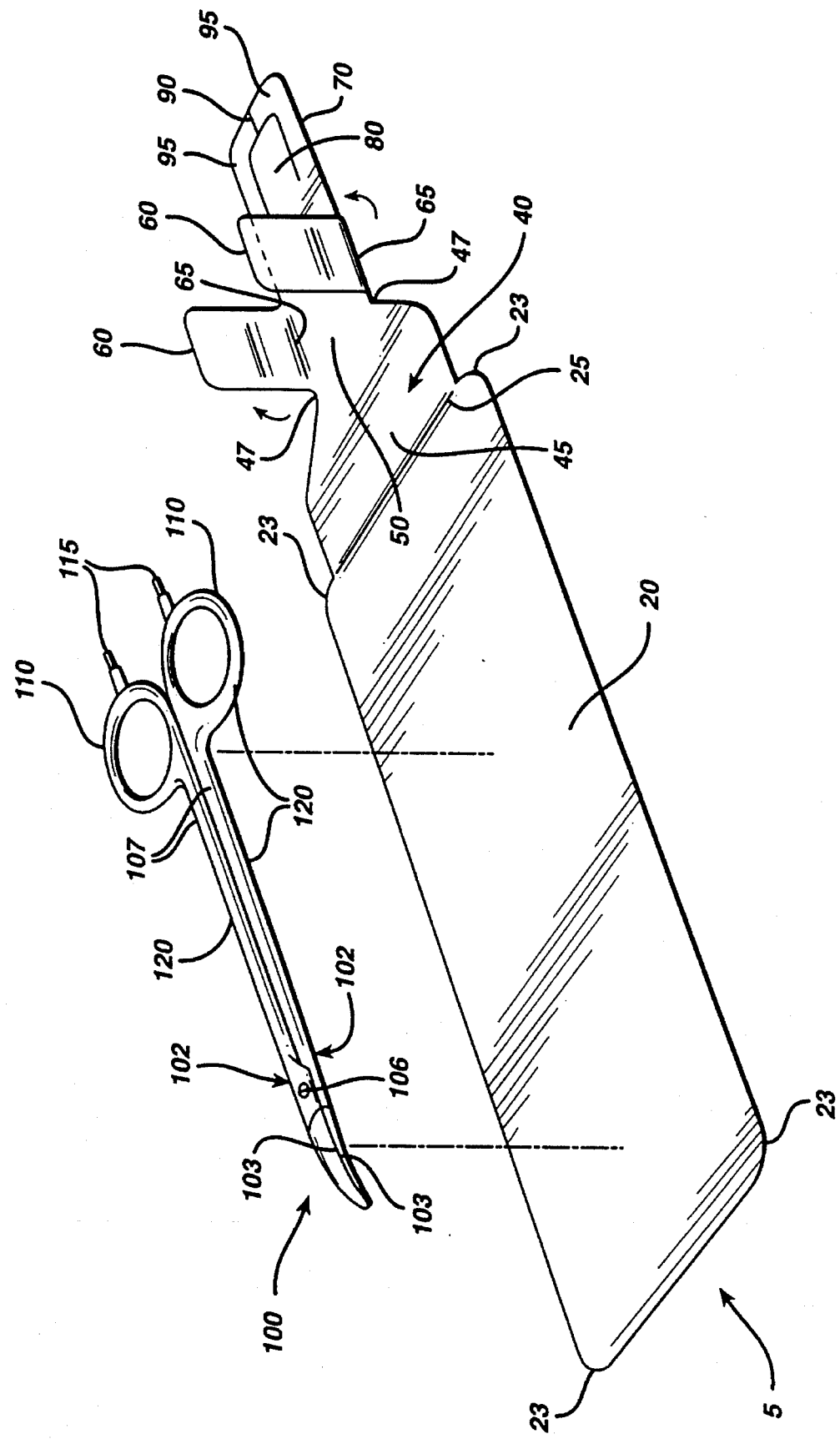
FIG. 3 is a perspective view of the package of the present invention prior to assembly also illustrating electrosurgical scissors.

The package 5 of the present invention is seen, prior to folding and assembly, in FIG. 1 and FIG. 3. The package 5 is seen to have base panel 20. Base panel 20 is seen to be a substantially rectangularly-shaped panel having a pair of opposed minor sides and a pair of opposed major sides. Panel 20 is seen to have rounded corners 23. Foldably connected to minor side 27 along fold line 25 is the scissors retention panel 40. It is preferred that fold line 25 be a conventional crushed fold line, although other conventional fold lines, including score lines, can also be used. Scissors retention panel 40 is seen to have irregularly-shaped base section 45 slanting inwardly on both sides toward the middle, intermediate section 50 forming opposed finger ring retention slots 47. Extending outwardly from either side of middle, intermediate section 50 of retention panel 40 are the finger ring tab panels 60. Each finger ring tab panel 60 is seen to have a pair of crushed score lines 65 and 66 substantially parallel to the longitudinal axis 7 of package 5. The score lines 65 and 66 divide tab 60 into first section 61 and second section 62. Extending distally from top section 55 of the panel 40 is the retention tab member 70. Tab member 70 is seen to be substantially rectangularly shaped and is further seen to have U-shaped slit 72. Slit 72 is seen to have leg sections 73 and bottom section 74. U-shaped slit 72 is seen to form tab member 80 and opening 85 in retention tab member 70. Tab member 80 is attached to tab member 70 along bottom section 82. At the top 78 of tab member 70 is the slit 90 which intersects the bottom 74 of U-shaped slit 72 thereby forming opposed L-shaped members 95. Slit 90 is preferably perpendicular to the bottom 74 of slit 72, although other angles of inclination may be used. It will be appreciated by those skilled in the art that the shape and configuration of the panels, tabs, openings and tab members of the package 5 may vary in accordance with the particular configuration of the scissors. For example, panels may have various geometric shapes including square, oval, rectangular circular, polyhedral, and combinations thereof. It will be also appreciated that the package 5 of the present invention can also be used to package conventional scissors in addition to electrosurgical scissors.

Referring to FIGS. 2 and 3, electrosurgical scissors 100 are seen. The electrosurgical scissors 100 are seen to have scissor blade members 102 which are rotatable connected by screw 106. Blade members 102 have distal shearing members 103. The blade members 102 are each seen to have finger ring members 110 extending from the proximal ends 107 of the blade members 102. Electrodes 115 are seen to extend distally from the finger ring members 110. The scissors are seen to have insulating coating 120 covering blade members 102 and finger ring members 110.

Figure 4:
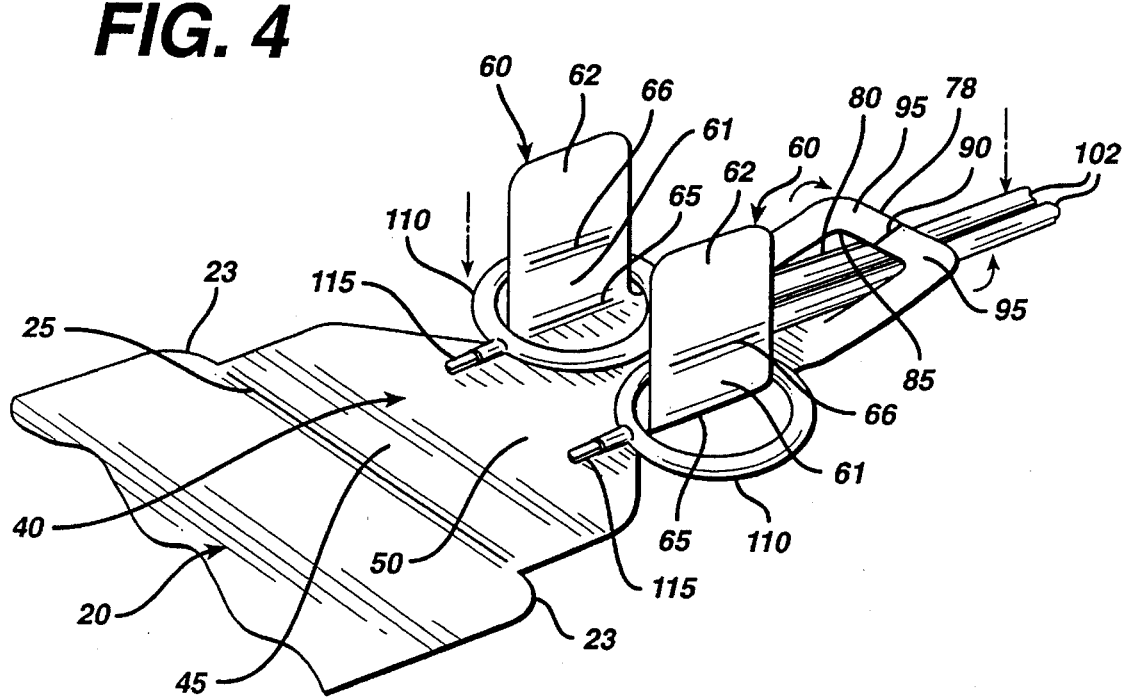
FIG. 4 is a partial perspective view of the package of the present invention illustrating the initial step in the assembly of the package.
Figure 5:
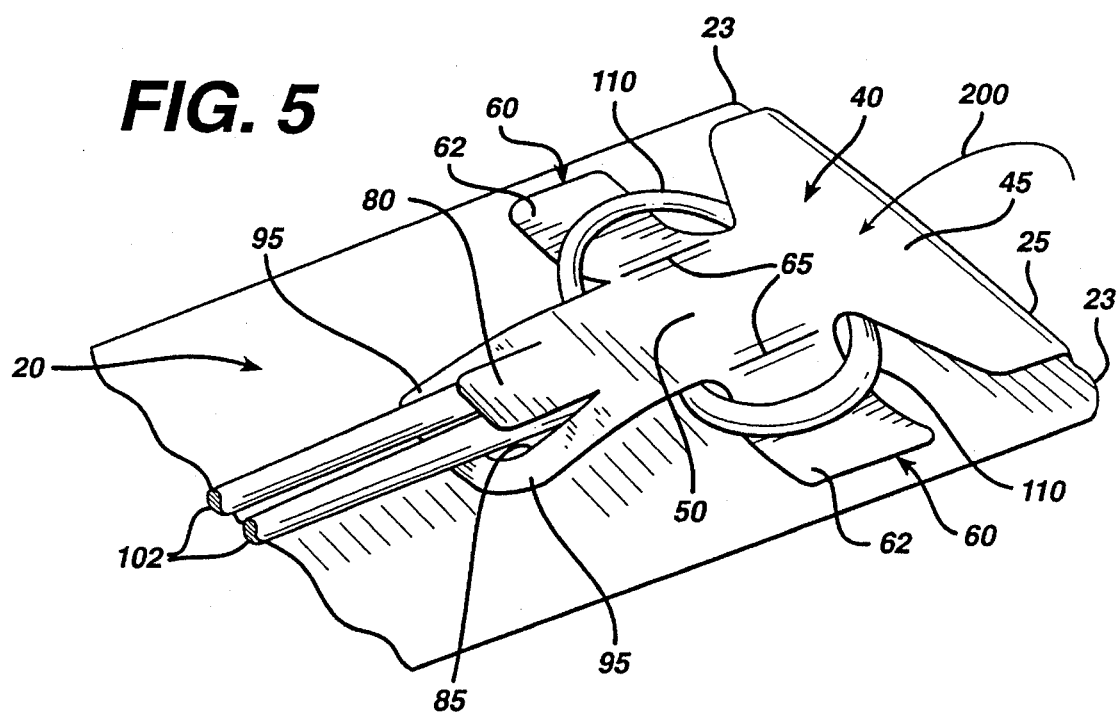
FIG. 5 is a partial perspective view of the top end of the package showing the final step in the assembly.

The assembly of the package 5 of the present invention is best illustrated in FIGS. 2,3,4, and 5. Referring to FIG. 4, the scissors 100 is laid upon retention panel 40, such that the tab members 60 are inserted through the ring members 110 such that tabs 60 are bent about crushed fold lines 65 and 66 as the tabs are inserted through rings 110. Then the L-shaped members 95 are separated and placed about the back of the scissor blades 102 thereby retaining the scissor blades 102 in opening 85 and between L-shaped members 95 and tab member 80. Next, the scissors retention panel containing the restrained scissors 100 is folded in a counter-clockwise manner with respect to arrow 200 such that the ends 62 of each tab 60 are resting upon the base panel 20. The assembled package 5 containing the scissors 100 may then be optionally inserted into an outer envelope or pouch 10 as seen in FIG. 2.

Conventional envelopes useful as outer envelope 10 may be made from polymer films including TYVEK®, polyester copolymers, polypropylene copolymers, polyethylene copolymers, combinations thereof, and the like. The envelopes 10 may also be made from polymer film, paper, and foil combinations. The folder packages 5 are preferably packaged in a conventional moisture proof foil envelope 10, such as a foil envelope, when used for bioabsorbable suture anchors and sutures. The envelopes 10 may if desired function as sterile barriers when conventionally sealed. The package 5 containing scissors 100 may be optionally sterilized using conventional sterilization processes.

The folder packages 5 of the present invention are preferably constructed from any material having the required structural characteristics such that the material can be readily die cut, and scored. In addition, the material must be easily folded and sterilizable. The materials include those known in the art for packaging sutures and medical devices, including paper, plastic, foils, and laminates of one or more thereof. However, it is particularly preferred in the practice of the present invention to utilize a heavyweight, relatively stiff, medical grade paper or paperboard such as, for example, 0.007–0.024" suture board.

The package 5 of the present invention has many advantages. It is easy to manufacture out of conventional materials. The package 5 is extremely easy to assemble. The package 5 is economical to manufacture and surprisingly and unexpectedly eliminates the need for extensive packing materials and bulky, heavy boxes or containers. Other advantages include protection of the scissors 100 in the package 5 from damage and shifting during shipping, handling and storage.

Although this invention has been shown and described in respect to detailed embodiments thereof, it will be understood by those skilled in the art the various changes in form and detail thereof may be made without departing from the spirit and scope of the claimed invention.

What is claimed is:

1. A foldable package for electrosurgical scissors, comprising:
   a base panel;
   a scissors retaining panel foldably connected to the base panel, the scissors retaining panel having a bottom section and an intermediate, middle section and a top, the bottom section having opposed notches for receiving finger rings of electrosurgical scissors;
   a pair of opposed tabs extending laterally outward from the middle section of the scissors retaining panel for retaining the finger rings of electrosurgical scissors, each tab member having a pair of fold lines dividing the tabs into inner and outer sections; and,
   a tab member extending distally from the top of the scissor retaining panel for retaining the blade members of an electrosurgical scissor, the tab member comprising a U-shaped slit forming a retention tab and an opening, and a slit in the top of the tab member intersecting the U-shaped slit thereby forming opposed L-shaped members in the tab member adjacent to the U-shaped slit.

2. A foldable package for electrosurgical scissors, comprising:
   a base panel;
   a scissors retaining panel foldably connected to the base panel, the scissors retaining panel having a bottom section and an intermediate, middle section and a top, the bottom section having opposed notches for receiving finger rings of electrosurgical scissors;
   means for retaining finger rings of electrosurgical scissors; and,
   means for retaining blade members of electrosurgical scissors.

3. The package of claim 2 wherein the means for retaining finger rings comprises a pair of opposed tabs extending laterally outward from the middle section of the scissors retaining panel, each tab member having a pair of fold lines dividing the tabs into inner and outer sections.

4. The package of claim 2 wherein the means for retaining blade members comprises a tab member extending distally from the top of the scissors retaining panel, the tab member comprising a U-shaped slit forming a retention tab and an opening, and a slit in the top of the tab member intersecting the U-shaped slit thereby forming opposed L-shaped members in the tab member adjacent to the U-shaped slit.

5. The package of claim 1 additionally comprising scissors.

6. The package of claim 2 additionally comprising scissors.

7. The package of claim 5 wherein the scissors comprise electrosurgical scissors.

8. The package of claim 6 wherein the scissors comprise electrosurgical scissors.

* * * * *